US007648960B2

(12) United States Patent
Steiner et al.

(10) Patent No.: US 7,648,960 B2
(45) Date of Patent: *Jan. 19, 2010

(54) METHOD FOR DELIVERY OF MONOMERIC OR DIMERIC INSULIN COMPLEXED TO DIKETOPIPERAZINE MICROPARTICLES

(75) Inventors: Solomon S. Steiner, Mount Kisco, NY (US); Rodney J. Woods, New Hampton, NY (US); Joseph W. Sulner, Paramus, NJ (US)

(73) Assignee: MannKind Corporation, Valencia, CA (US)

( * ) Notice: Subject to any disclaimer, the term of this patent is extended or adjusted under 35 U.S.C. 154(b) by 173 days.

This patent is subject to a terminal disclaimer.

(21) Appl. No.: 10/719,734

(22) Filed: Nov. 21, 2003

(65) Prior Publication Data
US 2004/0077528 A1 Apr. 22, 2004

Related U.S. Application Data

(60) Continuation of application No. 10/224,761, filed on Aug. 20, 2002, now Pat. No. 6,652,885, which is a division of application No. 09/606,468, filed on Jun. 29, 2000, now Pat. No. 6,444,226.

(60) Provisional application No. 60/141,433, filed on Jun. 29, 1999.

(51) Int. Cl.
*A61K 38/28* (2006.01)
*A61K 38/00* (2006.01)
*A61K 9/00* (2006.01)
*A61K 9/14* (2006.01)

(52) U.S. Cl. .............................. 514/3; 514/2; 424/489; 424/499; 424/46

(58) Field of Classification Search ................ 414/489; 424/43, 46, 489, 499; 514/2, 3
See application file for complete search history.

(56) References Cited

U.S. PATENT DOCUMENTS

| 3,906,950 A | 9/1975 | Cocozza |
| 3,921,637 A | 11/1975 | Bennie et al. |
| 4,153,689 A | 5/1979 | Hirai |
| 4,196,196 A | 4/1980 | Tiholiz |
| 4,211,769 A | 7/1980 | Okada |
| 4,272,398 A | 6/1981 | Jaffe |
| 4,294,829 A | 10/1981 | Suzuki |
| 4,659,696 A | 4/1987 | Hirai |
| 4,861,627 A | 8/1989 | Mathiowitz |
| 4,866,051 A | 9/1989 | Hunt |
| 4,946,828 A | 8/1990 | Markussen |
| 5,006,343 A | 4/1991 | Benson |
| 5,042,975 A | 8/1991 | Chien |
| 5,145,684 A | 9/1992 | Liversidge et al. |
| 5,188,837 A | 2/1993 | Domb |
| 5,204,108 A | 4/1993 | Illum |
| 5,260,306 A | 11/1993 | Boardman et al. |
| 5,352,461 A | 10/1994 | Feldstein et al. |
| 5,354,562 A | 10/1994 | Platz |
| 5,364,838 A | 11/1994 | Rubsamen |
| 5,458,135 A | 10/1995 | Patton et al. |
| 5,482,927 A | 1/1996 | Maniar |
| 5,484,606 A | 1/1996 | Dhabhar et al. |
| 5,492,112 A | 2/1996 | Mecikalski et al. |
| 5,503,852 A | 4/1996 | Steiner et al. |
| 5,514,646 A | 5/1996 | Chance et al. |
| 5,547,929 A | 8/1996 | Anderson, Jr. et al. |
| 5,562,909 A | 10/1996 | Allcock et al. |
| 5,577,497 A | 11/1996 | Mecikalski et al. |
| 5,653,961 A | 8/1997 | McNally et al. |
| 5,658,878 A | 8/1997 | Bäckström et al. |
| 5,693,338 A | 12/1997 | Milstein |

(Continued)

FOREIGN PATENT DOCUMENTS

EP 0/069/715 1/1983

(Continued)

OTHER PUBLICATIONS

Edelman, S.V. "Type II Diabetes Mellitus," Advances in Internal Medicine, 1998, 43, pp. 449-500 (Abstract Only).*
Cerasi, et al., "Decreased sensitivity of the pancreatic beta cells to glucose in prediabetic and diabetic subjects. A glucose dose-response study," *Diabetes* 21(4): 224-34 (1972).
Gupta, et al., "Contemporary approaches in aerosolized drug delivery to the lung," *Journal of Controlled Release* 17:129-148 (1991).
Katchalski, et al., "Synthesis of lysine anhydride," *J. Amer. Chem. Soc.* 68: 879-80 (1946).
Kopple, et al., "A convenient synthesis of 2,5-piperazinediones," *J. Org. Chem.* 33(2): 862-64 (1968).
Leahy, "Beta-cell dysfunction in type II diabetes mellitus," *Curr. Opin. Endocrinol. Diabetes* 2(4): 300-306 (1995).
Lian, et al., "A self-complementary, self-assembling microsphere system: application for intravenous delivery of the antiepileptic and neuroprotectant compound felbamate," *J Pharm Sci* 89:867-875 (2000).

(Continued)

*Primary Examiner*—Johann R Richter
*Assistant Examiner*—James H. Alstrum-Acevedo
(74) *Attorney, Agent, or Firm*—Louis C. Cullman; Michelle S. Glasky; K&L Gates LLP

(57) ABSTRACT

Methods are provided for purifying peptides and proteins by incorporating the peptide or protein into a diketopiperazine or competitive complexing agent to facilitate removal of one or more impurities from the peptide or protein. Formulations and methods also are provided for the improved transport of active agents across biological membranes, resulting for example in a rapid increase in blood agent concentration. The formulations include microparticles formed of (i) the active agent, which may be charged or neutral, and (ii) a transport enhancer that masks the charge of the agent and/or that forms hydrogen bonds with the target biological membrane in order to facilitate transport. In one embodiment insulin is administered via the pulmonary delivery of microparticles comprising fumaryl diketopiperazine and insulin in its biologically active form. This method of delivering insulin results in a rapid increase in blood insulin concentration that is comparable to the increase resulting from intravenous delivery.

11 Claims, 2 Drawing Sheets

U.S. PATENT DOCUMENTS

| | | | |
|---|---|---|---|
| 5,740,794 A | 4/1998 | Smith et al. |
| 5,747,445 A | 5/1998 | Bäckström et al. |
| 5,763,396 A | 6/1998 | Weiner et al. |
| RE35,862 E | 7/1998 | Steiner et al. |
| 5,785,049 A | 7/1998 | Smith et al. |
| 5,785,989 A | 7/1998 | Stanley et al. |
| 5,807,315 A | 9/1998 | Van Antwerp et al. |
| 5,849,322 A | 12/1998 | Ebert et al. |
| 5,874,064 A | 2/1999 | Edwards et al. |
| 5,877,174 A | 3/1999 | Ono et al. |
| 5,888,477 A | 3/1999 | Gonda et al. |
| 5,901,703 A | 5/1999 | Ohki et al. |
| 5,912,011 A | 6/1999 | Makino et al. |
| 5,929,027 A | 7/1999 | Takama et al. |
| 5,952,008 A | 9/1999 | Bäckström et al. |
| 5,976,569 A | 11/1999 | Milstein |
| 5,985,309 A | 11/1999 | Edwards et al. |
| 5,997,848 A | 12/1999 | Patton et al. |
| 6,051,256 A | 4/2000 | Platz et al. |
| 6,063,910 A | 5/2000 | Debenedetti |
| 6,071,497 A | 6/2000 | Steiner et al. |
| 6,099,517 A | 8/2000 | Daugherty |
| 6,131,567 A | 10/2000 | Gonda et al. |
| 6,153,613 A | 11/2000 | Ono et al. |
| RE37,053 E | 2/2001 | Hanes et al. |
| 6,254,854 B1 | 7/2001 | Edwards et al. |
| 6,294,204 B1 | 9/2001 | Rossling et al. |
| 6,331,318 B1 | 12/2001 | Milstein |
| 6,395,774 B1 | 5/2002 | Milstein |
| 6,423,344 B1 | 7/2002 | Platz et al. |
| 6,428,771 B1 | 8/2002 | Steiner et al. |
| 6,432,383 B1 | 8/2002 | Modi |
| 6,436,443 B2 | 8/2002 | Edwards et al. |
| 6,440,463 B1 | 8/2002 | Feldstein et al. |
| 6,447,753 B2 | 9/2002 | Edwards et al. |
| 6,503,480 B1 | 1/2003 | Edwards et al. |
| 6,518,239 B1 | 2/2003 | Kuo et al. |
| 6,582,728 B1 | 6/2003 | Platz |
| 6,592,904 B2 | 7/2003 | Platz et al. |
| 6,635,283 B2 | 10/2003 | Edwards et al. |
| 6,652,885 B2 | 11/2003 | Steiner et al. |
| 6,676,931 B2 | 1/2004 | Dugger, III. |
| 6,685,967 B1 | 2/2004 | Patton |
| 6,737,045 B2 | 5/2004 | Patton |
| 6,949,258 B2 | 9/2005 | Zhang |
| 7,030,084 B2 | 4/2006 | Ekwuribe et al. |
| 2003/0017211 A1 | 1/2003 | Steiner |
| 2003/0064097 A1 | 4/2003 | Patel et al. |
| 2003/0068378 A1 | 4/2003 | Chen et al. |
| 2003/0194420 A1 | 10/2003 | Holl et al. |
| 2004/0096403 A1 | 5/2004 | Steiner |
| 2004/0151774 A1 | 8/2004 | Pauletti et al. |
| 2004/0157928 A1 | 8/2004 | Jae-Hwan et al. |
| 2004/0182387 A1 | 9/2004 | Steiner |
| 2004/0247628 A1 | 12/2004 | Lintz et al. |
| 2005/0080000 A1 | 4/2005 | Horst et al. |
| 2005/0153874 A1 | 7/2005 | Cheatham |
| 2005/0214251 A1 | 9/2005 | Pohl et al. |
| 2007/0086952 A1 | 4/2007 | Steiner |

FOREIGN PATENT DOCUMENTS

| | | |
|---|---|---|
| EP | 0/122/036 | 10/1984 |
| EP | 0 220 958 | 5/1987 |
| EP | 0220958 A2 | 5/1987 |
| EP | 0/237/507 | 9/1987 |
| EP | 0 257 915 | 2/1988 |
| EP | 0/360/340 | 3/1990 |
| EP | 0/364/235 | 4/1990 |
| EP | 0606486 | 12/1993 |
| EP | 0655237 A1 | 5/1995 |
| EP | 0748213 | 12/1996 |
| EP | 1/114/644 | 7/2001 |
| GB | 2240337 | 7/1991 |
| JP | 63-020301 | 1/1988 |
| JP | 0149545 | 2/1992 |
| WO | WO 90/13285 | 11/1990 |
| WO | WO 91/04011 | 4/1991 |
| WO | WO 91/16882 | 11/1991 |
| WO | WO 92/04069 | 3/1992 |
| WO | WO 92/08509 | 5/1992 |
| WO | WO 93/02712 | 2/1993 |
| WO | 93/14110 A1 | 7/1993 |
| WO | WO 93/17728 | 9/1993 |
| WO | WO 93/18754 | 9/1993 |
| WO | WO 94/00291 | 1/1994 |
| WO | 94/08599 A1 | 4/1994 |
| WO | 94/23702 A1 | 10/1994 |
| WO | WO 95/00127 | 1/1995 |
| WO | WO 95/11666 | 5/1995 |
| WO | WO 95/31979 | 11/1995 |
| WO | WO 95/34294 | 12/1995 |
| WO | 96/05810 A1 | 2/1996 |
| WO | 96/36314 A2 | 11/1996 |
| WO | WO 96/36314 | 11/1996 |
| WO | 97/04747 A1 | 2/1997 |
| WO | WO 97/49386 | 12/1997 |
| WO | 99/33862 A1 | 7/1999 |
| WO | WO 99/52506 | 10/1999 |
| WO | WO 01/00654 | 1/2001 |
| WO | WO 01/07107 | 2/2001 |
| WO | WO 02/11676 | 2/2002 |
| WO | WO 03/057170 | 7/2003 |
| WO | WO 03/086345 | 10/2003 |
| WO | WO 03/094951 | 11/2003 |
| WO | WO 2004/056314 | 7/2004 |
| WO | WO 2004/075919 | 9/2004 |
| WO | WO 2005/089722 | 9/2005 |

OTHER PUBLICATIONS

Pfeiffer, "Insulin secretion in diabetes mellitus," *Am. J. Med.* 70(3): 579-88 (1981).

Polonsky, et al., "Abnormal patterns of insulin secretion in non-insulin-dependent diabetes mellitus," *N. England J. Med.* 318(19): 1231-39 (1988).

Jones, et al., "An investigation of the pulmonary absorption of insulin in the rat", *Third European Congress of Biopharmaceutics and Pharmacokinetics*, 1987.

Sakr, "A new approach for insulin delivery via the pulmonary route: design and pharmacokinetics in non-diabetic rabbits", *International Journal of Pharmaceutics*, 86:1-7 (1992).

Benita, "Characterization of Drug-Loaded Poly(d,l-lactide) Microspheres," *J. Pharm. Sci.*, 73: 1721-1724 (1984).

Bensch, et al., "Absorption of intact protein molecules across the pulmonary air-tissue barrier," *Science* 156: 1204-1206 (1967).

Brange, et al., "Insulin Structure and stability", *Pharm Biotechnol.*, 5:315-50 (1993).

Cefalu, et al, "Inhaled Human Insulin Treatment in Patients with type 2 diabetes mellitus," *Ann. Int. Med.*, 134: 203-7 (2001).

Cheatham and Pfeutzner, "Desirable dynamics & performance of inhaled insulin compared to subcutaneous insulin given at mealtime in type 2 diabetes: A report from the technosphere/insulin study group" *Diabetes Technology & Therapeutics* 6:234-235 (2004).

Costello, et al., "Zinc inhibition of mitochondrial aconitase and its importance in citrate metabolism in prostate epithelial cells", *Journ. Biol. Chem.*, 272(46):28875-28881 (1997).

Dieter Köhler, "Aerosols for Systemic Treatment", *Lung (Suppl)*, 677-684 (1990).

Dunn, "Zinc-ligand interactions modulate assembly and stability of the insulin hexamer", *Biometals*, 18(4):295-303 (2005).

Elliott, et al., "Parenteral absorption of insulin from the lung in diabetic children," *Austr. Paediat. J.* 23: 293-297 (1987).

Engelgau, et al., "Screening for type 2 diabetes," *Diabetes Care* 1563(23):1-31 (2000).
Festa, et al., "LDL particle size in relation to insulin, proinsulin, and insulin sensitivity" *Diabetes Care* 22(10):1688-1693 (1999).
Garber, "Premixed insulin analogues for the treatment of diabetes mellitus", *Drugs*, 66(1):31-49 (2006).
Haffner, et al., "Proinsulin and insulin concentrations 1 relation to carotid wall thickness" *Stroke* 29:1498-1503 (1998).
Hagedorn, et al., "Protamine insulin", *JAMA*, 106:177-180 (1936).
Hanley et al., "Cross-sectional and prospective associations between proinsulin and cardiovascular disease risk factors in a population experiencing rapid cultural transition" *Diabetes Care* 24(7):1240-1247 (2001).
Heyder, "Alveolar deposition of inhaled particles in humans," *Am. Ind. Hyg. Assoc. J.* 43(11): 864-866 (1982).
Heyder, "Particle Transport onto Human Airway Surfaces" *Eur. J. Respir. Dis. Suppl. 119*, 29-50 (1982).
Johnson, et al., "Turbuhaler® : a new device for dry powder terbutaline inhalation," *Allergy* 43(5):392-395 (1988).
Schluter, K. J. et al., "Pulmonary Administration . . . ," Abstract 298, *Diabetes* 33 (Suppl.):75A (1984).
Kohler, "Aerosols for Systemic Treatment", *Lung Suppl.* 677-683 (1990).
Komada, et al., "Intratracheal delivery of peptide and protein agents: absorption from solution and dry powder by rat lung," *J. Pharm. Sci.* 83(6): 863-867 (1994).
Kontny, et al. "Issues Surrounding MDI Formulation Development with Non-CFC Propellants," *J. Aerosol Med.* 4(3), 181-187 (1991).
Lee, et al., "Development of an Aerosol Dosage Form Containing Insulin," *J. Pharm. Sci.* 65(4), 567-572 (1976).
Lim, "Microencapsulation of Living Cells and Tissues," *J. Pharm. Sci.* 70: 351-354 (1981).
Mathiowitz, "Morphology of Polyanhydride Microsphere Delivery Systems," *Scanning Microscopy*, 4: 329-340 (1990).
Mathiowitz, "Novel Microcapsules for Delivery Systems," *Reactive Polymers*, 6: 275-283 (1987).
Mathiowitz, "Polyanhydride Microspheres As Drug Carriers I. Hot-Melt Microencapsulation," *J. Controlled Release*, 5: 13-22 (1987).
Mathiowitz, "Polyanhydride Microspheres As Drug Carriers II. Microencapsulation by Solvent Removal," *J. Applied Poly. Sci.*, 35: 755-774 (1988).
Mathiowitz, "Polyanhydride Microspheres IV.Morpohology and Characterization of Systems Made by Spray Drying," *J. Applied Poly. Sci.*, 45: 125-134 (1992).
Moren, *Aerosols in Medicine*, (2nd ed.), Elsevier, pp. 321-350.
Nagai, et al., "Powder Dosage Form of Insulin for Nasal Administration," *J. Control Rel.*, 1:15-22 (1984).
Okumura, et al., "Intratracheal delivery of insulin. Absorption from solution and aerosol by rat lung," *Int. J. Pharmaceuticals* 88: 63-73 (1992).
Patton & Platz, "Routes of Delivery: Case Studies. Pulmonary delivery of peptides and proteins for systemic action," *Adv. Drug. Del. Rev.* 8: 179-196 (1992).
Pfutzner, et al., "Influence of small dose i.v., s.c. and pulmonary insulin treatment on prandial glucose control in patients with type 2 diabetes" *37th Annual Meeting of the EASD, Glasgow*, Sep. 9-13, 2001 812 (2001) (abstract).
Prabhu, et al. "A study of factors controlling dissolution kinetic of zinc complexed protein suspensions in various ionic species", *Int. J. Pharm.*, 217(1-2):71-8 (2001).
Raskin, et al., "Continuous subcutaneous insulin infusion and multiple daily injection therapy are equally effective in type 2 diabetes" *Diabetes Care* 26:2598-2603 (2003).
Rosenstock, et al., "Reduced hypoglycemia risk with insulin glargine: a meta-analysis comparing insulin glargine with human NPH insulin in type 2 diabetes", Diabetes Care, 28(4):950-5 (2005).
Salib, "Utilization of Sodium Alginate in Drug Microencapsulation," *Pharazeutische Industrie* , 40(11a): 1230-1234 (1978).
Sawhney, "Bioerodible Hydrogels Based on Photopolymerized Poly-(ethylene glycol)-co-poly(a-hydroxy acid) Diacrylate Macromers," *Macromolecules*, 26: 581-587 (1993).
Schluter, et al., "Pulmonary Administration of Human Insulin in Volunteers and Type I Diabetics", *Diabetes*, 33 (Suppl.): 298 (1984).

Schneider, et al., "Stimulation by proinsulin of expression of plasminogen activator inhibitor type-I in endothelial cells" *Diabetes* 41(7):890-895 (1992).
Warren, et al., "Postprandial versus preprandial dosing of biphasic insulin aspart in elderly type 2 diabetes patients" *Diabetes Research and Clinical Practive* 66:23-29 (2004).
Waterhouse, et al. "Comparative assessment of a new breath-actuated inhaler in patients with reversible airways obstruction." *Respiration* 59:155-158 (1992).
Wigley, et al., "Insulin across respiratory mucosae by aerosol delivery," *Diabetes* 20(8): 552-556 (1971).
Witchert, "Low Molecular Weight PLA: A Suitable Polymer for Pulmonary Administered Microparticles," *J. Microencapsulation*, 10(2): 195-207 (1993).
Yoshida, et al., "Absorption of insulin delivered to rabbit trachea using aerosol dosage form," *J. Pharm. Sci.* 68(5): 670-671 (1979).
Zethelius, et al., "Proinsulin is an Independent Predictor of Coronary Heart Disease" *Circulation* 105:2153-2158 (2002).
Berge, et al. "Pharmaceutical Salts," *J. Pharmaceutical Sciences* 66(1):1-19 (1997).
Heinemann, et al. "Current Status of the development of inhaled insulin" *Br. J. Diabetes Vasc Dis* 4:295-301 (2004).
Steiner, et al. "Technosphere ™/ Insulin- proof of concept study with new insulin formulation for pulmonary delivery" *Exp. Clin. Endocrinol. Diabetes* 110:17-21 (2002).
Kohler, et al. "Non-radioactive approach for measuring lung permeability: inhalation of insulin," *Atemw Lungebkrkh* 13:230-232 (1987). (Original in German and English Translation attached).
Bauer K et al. "Pharmacodynamic effects of inhaled dry powder formulations of fenterol and colforsin in asthma." Clin Pharmacol Ther 53:76-83, 1993.
Raz I et al. "Pharmacodynamics and pharmacokinetics of dose ranging effects of Oralin versus s.c. regular insulin in Type 1 diabetic subjects." Fourth Annual Diabetes Technology Meeting, Abstract, 2004.
Heubner W et al. "On inhalation of insulin." Klinische Wochenschrift 3:2342-2343, 1924. Original in German. English translation attached.
Liu Fy et al. "Pulmonary delivery of free and liposomal insulin." Pharmaceutical Res. 10:228-232, 1993.
Petkowicz J et al. "Hypoglycemic effect of liposome-entrapped insulin administered by various routes into normal rats." Pol. J. Pharmacol. Pharm. 41:299-304, 1989.
Sarrach D et al. "Binding and entrapment of insulin by liposomes made of lecithin-phosphotidic acid in acid solution." Pharmazie 40:642-645, 1985. In German with English Abstract.
Schroder U "Crystallized carbohydrate spheres as a slow release matrix for biologically active substances." Biomaterials 5:100-104, 1984.
Kohler, "Aerosols for Systemic Treatment", *Lung Suppl.* 677-683 (1990).
Komada, et al., "Intratracheal delivery of peptide and protein agents: absorption from solution and dry powder by rat lung," *J. Pharm. Sci.* 83(6): 863-867 (1994).
Kontny, et al."Issues Surrounding MDI Formulation Development with Non-CFC Propellants," *J. Aerosol Med.* 4(3), 181-187(1991).
Lee, et al., "Development of an Aerosol Dosage Form Containing Insulin, " *J. Pharm. Sci.* 65(4), 567-572 (1976).
Lim, "Microencapsulation of Living Cells and Tissues," *J. Pharm. Sci.*, 70: 351-354 (1981).
Mathiowitz, "Morphology of Polyanhydride Microsphere Delivery Systems," *Scanning Microscopy*, 4: 329-340 (1990).
Mathiowitz, "Novel Microcapsules for Delivery Systems," *Reactive Polymers*, 6: 275-283 (1987).
Mathiowitz, "Polyanhydride Microspheres As Drug Carriers I. Hot-Melt Microencapsulation," *J. Controlled Release*, 5: 13-22(1987).
Mathiowitz, "Polyanhydride Microspheres As Drug Carriers II. Microencapsulation by Solvent Removal," *J. Applied Poly. Sci.*, 35: 755-774 (1988).
Mathiowitz, "Polyanhydride Microspheres IV.Morpohology and Characterization of Systems Made by Spray Drying," *J. Applied Poly. Sci.*, 45: 125-134 (1992).
Moren, *Aerosols in Medicine*, (2nd ed.), Elsevier, pp. 321-350, 1993.

\* cited by examiner

METHOD FOR DELIVERY OF MONOMERIC OR DIMERIC INSULIN COMPLEXED TO DIKETOPIPERAZINE MICROPARTICLES

CROSS-REFERENCE TO RELATED APPLICATIONS

This application is a continuation of U.S. Ser. No. 10/224,761 filed on Aug. 20, 2002, which is a divisional of U.S. Ser. No. 09/606,468 filed Jun. 29, 2000 (now U.S. Pat. No. 6,444,226), which claims the benefit of U.S. Ser. No. 60/141,433, filed Jun. 29, 1999.

BACKGROUND OF THE INVENTION

The present invention is generally in the field of pharmaceutical formulations, and more particularly related to methods and compositions for purifying and stabilizing peptides and proteins, such as insulin, which are used in pharmaceutical applications.

In a normal person, the β-cells of the pancreatic islets of Langerhans produce insulin, required by the body for glucose metabolism, in response to an increase in blood glucose concentration. The insulin metabolizes incoming glucose and temporarily stops the liver's conversion of glycogen and lipids to glucose thereby allowing the body to support metabolic activity between meals. The Type I diabetic, however, has a reduced ability or absolute inability to produce insulin due to β-cell destruction and needs to replace the insulin via daily injections or an insulin pump. More common than Type I diabetes, though, is Type II diabetes, which is characterized by insulin resistance and increasingly impaired pancreatic β-cell function. Type II diabetics may still produce insulin, but they may also require insulin replacement therapy.

Type II diabetics typically exhibit a delayed response to increases in blood glucose levels. While normal persons usually release insulin within 2-3 minutes following the consumption of food, Type II diabetics may not secrete endogenous insulin for several hours after consumption. As a result, endogenous glucose production continues after consumption (Pfeiffer, *Am. J. Med.*, 70:579-88 (1981)), and the patient experiences hyperglycemia due to elevated blood glucose levels.

Loss of glucose-induced insulin secretion is one of the earliest disturbances of β-cell function (Cerasi et al., *Diabetes*, 21:224-34 (1972); Polonsky et al., *N. Engl. J. Med.*, 318:1231-39 (1988)), but the causes and degree of β cell dysfunction are unknown in most cases. While genetic factors play an important role, (Leahy, *Curr. Opin. Endocrinol. Diabetes*, 2:300-06 (1995)), some insulin secretory disturbances seem to be acquired and may be at least partially reversible through optimal glucose control. Optimal glucose control via insulin therapy after a meal can lead to a significant improvement in natural glucose-induced insulin release by requiring both normal tissue responsiveness to administered insulin and an abrupt increase in serum insulin concentrations. Therefore, the challenge presented in the treatment of early stage Type II diabetics, those who do not have excessive loss of β-cell function, is to restore the release of insulin following meals.

Most early stage Type II diabetics currently are treated with oral agents, but with little success. Subcutaneous injections of insulin are also rarely effective in providing insulin to Type II diabetics and may actually worsen insulin action because of delayed, variable, and shallow onset of action. It has been shown, however, that if insulin is administered intravenously with a meal, early stage Type II diabetics experience the shutdown of hepatic glucogenesis and exhibit increased physiological glucose control. In addition, their free fatty acids levels fall at a faster rate than without insulin therapy. While possibly effective in treating Type II diabetes, intravenous administration of insulin, is not a reasonable solution, as it is not safe or feasible for patients to intravenously administer insulin at every meal.

Insulin, a polypeptide with a nominal molecular weight of 6,000 Daltons, traditionally has been produced by processing pig and cow pancreas to isolate the natural product. More recently, however, recombinant technology has been used to produce human insulin in vitro. Natural and recombinant human insulin in aqueous solution is in a hexameric configuration, that is, six molecules of recombinant insulin are non-covalently associated in a hexameric complex when dissolved in water in the presence of zinc ions. Hexameric insulin is not rapidly absorbed. In order for recombinant human insulin to be absorbed into a patient's circulation, the hexameric form must first dissociate into dimeric and/or monomeric forms before the material can move into the blood stream. The delay in absorption requires that the recombinant human insulin be administered approximately one half hour prior to meal time in order to produce therapeutic insulin blood level, which can be burdensome to patients who are required to accurately anticipate the times they will be eating. To overcome this delay, analogs of recombinant human insulin, such as HUMALOG™, have been developed, which rapidly disassociate into a virtually entirely monomeric form following subcutaneous administration. Clinical studies have demonstrated that HUMALOG™ is absorbed quantitatively faster than recombinant human insulin after subcutaneous administration. See, for example, U.S. Pat. No. 5,547,929 to Anderson Jr., et al.

In a effort to avoid the disadvantages associated with delivery by injection and to speed absorption, administration of monomeric analogs of insulin via the pulmonary route has been developed. For example, U.S. Pat. No. 5,888,477 to Gonda, et al. discloses having a patient inhale an aerosolized formulation of monomeric insulin to deposit particles of insulin on the patient's lung tissue. However, the monomeric formulation is unstable and rapidly loses activity, while the rate of uptake remains unaltered.

While it would be desirable to produce rapidly absorbable insulin derived from natural sources, transformation of the hexameric form into the monomeric form, such as by removing the zinc from the complex, yields an insulin that is unstable and has an undesirably short shelf life. It therefore would be desirable to provide monomeric forms of insulin, while maintaining its stability in the absence of zinc. It also would be advantageous to provide diabetic patients with monomeric insulin compositions that are suitable for pulmonary administration, provide rapid absorption, and which can be produced in ready-to-use formulations that have a commercially useful shelf-life.

These problems with impurities, metal ions that affect stability or bioavailability, occur with many other proteins and peptides.

U.S. Pat. No. 6,071,497 to Steiner, et al. discloses microparticle drug delivery systems in which the drug is encapsulated in diketopiperazine microparticles which are stable at a pH of 6.4 or less and unstable at pH of greater than 6.4, or which are stable at both acidic and basic pH, but which are unstable at pH between about 6.4 and 8. The patent does not describe monomeric insulin compositions that are suitable for pulmonary administration, provide rapid absorption, and which can be produced in ready-to-use formulations that have a commercially useful shelf-life.

It would therefore be advantageous to develop alternative insulin delivery compositions for Type II diabetics that provide more rapid elevation of insulin blood levels and are easily administered to ensure patient compliance. It also would be desirable to apply the delivery compositions and methods to other biologically active agents.

It is therefore an object of the present invention to provide improved methods for purifying peptides and proteins, especially in the preparation of compositions suitable for pulmonary administration.

It is another object of the present invention to provide stable monomeric peptide compositions suitable for pulmonary delivery.

It is a further object of the present invention to provide methods and compositions for the facilitated transport of insulin and other biologically active agents across biological membranes.

It is another object of the present invention to provide methods and compositions for the improved absorption of insulin or other biologically active agents in the bloodstream.

It is a still further object of the present invention to provide methods and compositions for the improved absorption of insulin or other biologically active agents in the bloodstream characterized by ease of administration.

SUMMARY OF THE INVENTION

Methods are provided for purifying peptides and proteins by incorporating the peptide or protein into a diketopiperazine or competitive complexing agent to facilitate removal one or more impurities, i.e. undesirable components, from the peptide or protein. In a preferred embodiment, a peptide, such as insulin, containing one or more impurities, e.g., zinc ions, is entrapped in diketopiperazine to form a precipitate of peptide/diketopiperazine/impurity, which is then washed with a solvent for the impurity to be removed, which is a nonsolvent for the diketopiperazine and a nonsolvent for the peptide. Alternatively, the impurity can be removed by using complexing agents to selectively complex with and displace the impurities, for example, such as by dialysis.

Formulations and methods also are provided for the improved transport of active agents across biological membranes, resulting, for example, in a rapid increase in blood agent concentration. The formulations include microparticles formed of (i) the active agent, which may be charged or neutral, and (ii) a transport enhancer that masks the charge of the agent and/or that forms hydrogen bonds with the target biological membrane in order to facilitate transport. In a preferred embodiment, insulin is administered via pulmonary delivery of microparticles comprising fumaryl diketopiperazine and insulin in its biologically active form. The charge on the insulin molecule is masked by hydrogen bonding it to the diketopiperazine, thereby enabling the insulin to pass through the target membrane. This method of delivering insulin results in a rapid increase in blood insulin concentration that is comparable to the increase resulting from intravenous delivery.

DETAILED DESCRIPTION OF THE INVENTION

Figure 1A:
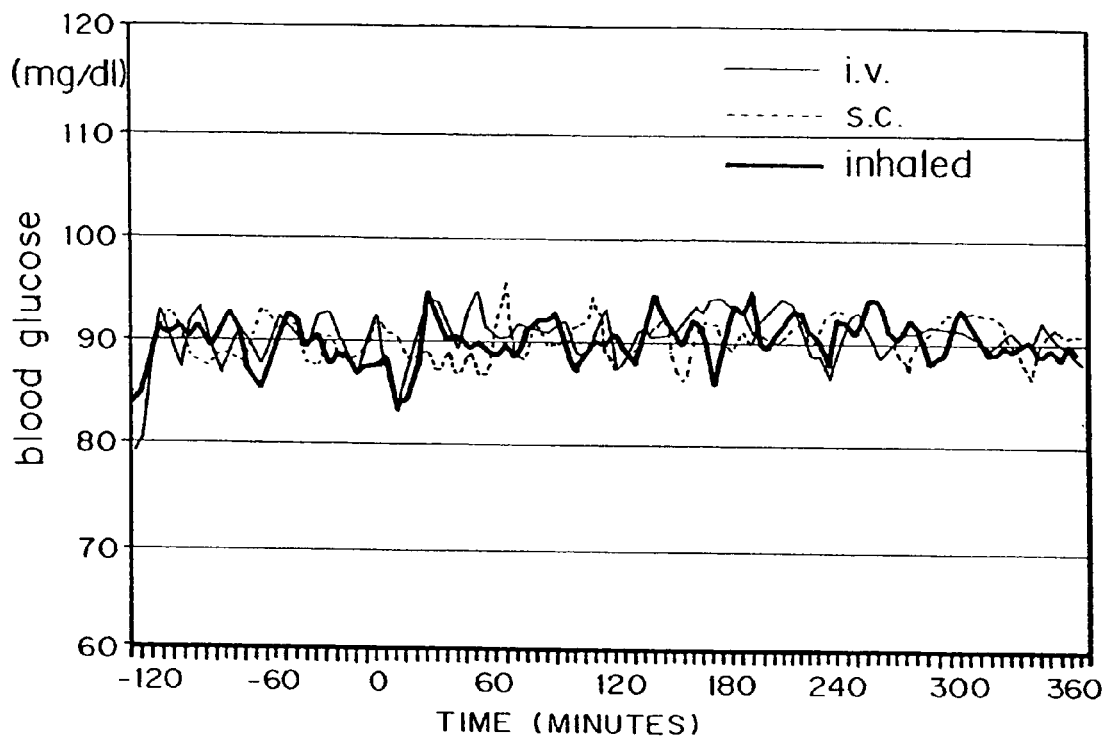
FIG. 1a is a graph of mean blood glucose values over time (minutes).

Encapsulation or entrapment of large polymers, such as proteins and peptides, in diketopiperazines can be used to remove impurities or contaminants such as metal ions or other small molecules. The diketopiperazines also serve both to stabilize and enhance delivery of the entrapped materials. Formulations also have been developed for the enhanced transport of active agents across biological membranes. These formulations include microparticles formed of (i) the active agent, which may be charged or neutral, and (ii) a transport enhancer that masks the charge of the agent and/or that forms hydrogen bonds with the membrane. The formulations can provide rapid increases in the concentration of active agent in the blood following administration of the formulations.

For example, it was discovered that hexameric insulin can be delivered to the lung in fumaryl diketopiperazine formulation, reaching peak blood concentrations within 3-10 minutes. In contrast, insulin administered by the pulmonary route without fumaryl diketopiperazine typically takes between 25-60 minutes to reach peak blood concentrations, while hexameric insulin takes 30-90 minutes to reach peak blood level when administered by subcutaneous injection. This feat has been successfully replicated several times and in several species, including humans.

Removing zinc from insulin typically produces unstable insulin with an undesirably short shelf life. Purification to remove zinc, stabilization and enhanced delivery of insulin is demonstrated by the examples. Formulations of insulin trapped in fumaryl diketopiperazine were found to be stable and have an acceptable shelf life. Measurement of the zinc levels demonstrated that the zinc had been largely removed during the entrapment process, yielding monomeric insulin in a stable delivery formulation.

Rapid absorption of a number of other peptides, including salmon calcitonin, parathyroid hormone 1-34, octreotide, leuprolide and RSV peptide, has been observed when the peptide is pulmonarily delivered in fumaryl diketopiperazine—providing peak blood concentrations within 3-10 minutes after pulmonary delivery.

I. Materials

A. Agent to be Delivered

The agent to be delivered is referred to herein as the active agent, or molecule to be encapsulated or entrapped. It may or may not be a charged species. Examples of classes of active agents suitable for use in the compositions and methods described herein include therapeutic, prophylactic, and diagnostic agents, as well as dietary supplements, such as vitamins.

The exact mechanism by which the diketopiperazines form a complex with the materials to be delivered is not known, but it is believed that the diketopiperazines form a complex with the material to be purified. This process is referred to herein interchangeably as entrapment or encapsulation.

These materials can be any polymer or large organic molecules, most preferably peptides and proteins. Generally speaking, any form of drug can be entrapped. Examples include synthetic inorganic and organic compounds, proteins and peptides, polysaccharides and other sugars, lipids, and nucleic acid sequences having therapeutic, prophylactic or diagnostic activities. Proteins are defined as consisting of 100 amino acid residues or more; peptide are less than 100 amino acid residues. Unless otherwise stated, the term protein refers to both proteins and peptides. The agents to be incorporated can have a variety of biological activities, such as vasoactive agents, neuroactive agents, hormones, anticoagulants, immunomodulating agents, cytotoxic agents, antibiotics, antivirals, antisense, antigens, and antibodies. In some instances, the proteins may be antibodies or antigens which otherwise would have to be administered by injection to elicit an appropriate response. Representative polymers including proteins, peptides, polysaccharides, nucleic acid molecule, and combinations thereof.

Preferred peptides and proteins include hormones, cytokines and other immunomodulatory peptides, and antigens/vaccines. In a preferred embodiment, the active agent is monomeric insulin or a stabilized form of insulin which has been purified to remove zinc. In another preferred embodiment, the active agent is glucagon.

The active agent, or drug, can be an antigen, where the molecule is intended to elicit a protective immune response, especially against an agent that preferentially infects the lungs, such as mycoplasma, bacteria causing pneumonia, and respiratory syncitial virus. In these cases, it may also be useful to administer the drug in combination with an adjuvant, to increase the immune response to the antigen.

Any genes that would be useful in replacing or supplementing a desired function, or achieving a desired effect such as the inhibition of tumor growth, could be introduced using the matrices described herein. As used herein, a "gene" is an isolated nucleic acid molecule of greater than thirty nucleotides, preferably one hundred nucleotides or more, in length. Examples of genes which replace or supplement function include the genes encoding missing enzymes such as adenosine deaminase (ADA) which has been used in clinical trials to treat ADA deficiency and cofactors such as insulin and coagulation factor VIII. Genes which effect regulation can also be administered, alone or in combination with a gene supplementing or replacing a specific function. For example, a gene encoding a protein which suppresses expression of a particular protein-encoding gene, or vice versa, which induces expresses of a protein-encoding gene, can be administered in the matrix. Examples of genes which are useful in stimulation of the immune response include viral antigens and tumor antigens, as well as cytokines (tumor necrosis factor) and inducers of cytokines (endotoxin), and various pharmacological agents.

Other nucleic acid sequences that can be utilized include antisense molecules which bind to complementary DNA to inhibit transcription, ribozyme molecules, and external guide sequences used to target cleavage by RNAase P.

As used herein, vectors are agents that transport the gene into targeted cells and include a promoter yielding expression of the gene in the cells into which it is delivered. Promoters can be general promoters, yielding expression in a variety of mammalian cells, or cell specific, or even nuclear versus cytoplasmic specific. These are known to those skilled in the art and can be constructed using standard molecular biology protocols. Vectors increasing penetration, such as lipids, liposomes, lipid conjugate forming molecules, surfactants, and other membrane permeability enhancing agents are commercially available and can be delivered with the nucleic acid.

Imaging agents including metals, radioactive isotopes, radioopaque agents, fluorescent dyes, and radiolucent agents also can be incorporated. Examples of radioisotopes and radioopaque agents include gallium, technetium, indium, strontium, iodine, barium, and phosphorus.

Impurities which can be removed from the active agent composition include metal ions such as zinc, and other di- or multi-valent ions, and small inorganic molecules and solvent residuals.

B. Diketopiperazines

Diketopiperazines useful in the present compositions and methods are described, for example, in U.S. Pat. No. 6,071,497, which is incorporated herein in its entirety.

(i). General Formula

The diketopiperazines or their substitution analogs are rigid planar rings with at least six ring atoms containing heteroatoms and unbonded electron pairs. One or both of the nitrogens can be replaced with oxygen to create the substitution analogs diketomorpholine and diketodioxane, respectively. Although it is possible to replace a nitrogen with a sulfur atom, this does not yield a stable structure.

The general formula for diketopiperazine and its analogs is shown below.

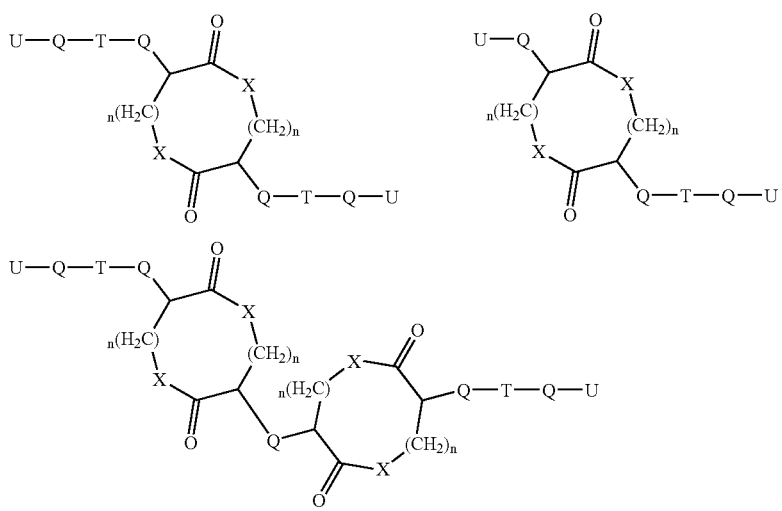

-continued

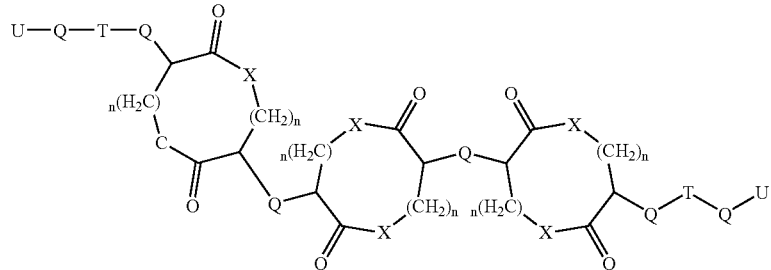

Wherein n is between 0 and 7, Q is, independently, a $C_{1-20}$ straight, branched or cyclic alkyl, aralkyl, alkaryl, alkenyl, alkynyl, heteroalkyl, heterocyclic, alkyl-heterocyclic, or heterocyclic-alkyl; T is —C(O)O, —OC(O), —C(O)NH, —NH, —NQ, —OQO, —O, —NHC(O), —OP(O), —P(O)O, —OP $(O)_2$, —P(O)$_2$O, —OS(O)$_2$, or —S(O)$_3$; U is an acid group, such as a carboxylic acid, phosphoric acid, phosphonic acid and sulfonic acid, or a basic group, such as primary, secondary and tertiary amines, quaternary ammonium salts, guanidine, aniline, heterocyclic derivatives, such as pyridine and morpholine, or a zwitterionic $C_{1-20}$ chain containing at least one acidic group and at least one basic group, for example, those described above, wherein the side chains can be further functionalized with an alkene or alkyne group at any position, one or more of the carbons on the side chain can be replaced with an oxygen, for example, to provide short polyethylene glycol chains, one or more of the carbons can be functionalized with an acidic or basic group, as described above, and wherein the ring atoms X at positions 1 and 4 are either O or N.

As used herein, "side chains" are defined as Q—T—Q—U or Q—U, wherein Q, T, and U are defined above.

Examples of acidic side chains include, but are not limited, to cis and trans —CH═CH—CO$_2$H, —CH(CH$_3$)═CH (CH$_3$)—CO$_2$H, —(CH$_2$)$_3$—CO$_2$H, —CH$_2$CH(CH$_3$)—CO$_2$H, —CH(CH$_2$CO$_2$H)═CH$_2$, -(tetrafluoro)benzoic acid, -benzoic acid and —CH(NHC(O)CF$_3$)—CH$_2$—CO$_2$H.

Examples of basic side chains include, but are not limited to, -aniline, -phenyl-C(NH)NH$_2$, -phenyl-C(NH)NH(alkyl), -phenyl-C(NH)N(alkyl)$_2$ and —(CH$_2$)$_4$NHC(O)CH(NH$_2$)CH(NH$_2$)CO$_2$H.

Examples of zwitterionic side chains include, but are not limited to, —CH(NH$_2$)—CH$_2$—CO$_2$H and —NH(CH$_2$)$_{1-20}$ CO$_2$H.

The term aralkyl refers to an aryl group with an alkyl substituent.

The term heterocyclic-alkyl refers to a heterocyclic group with an alkyl substituent.

The term alkaryl refers to an alkyl group that has an aryl substituent.

The term alkyl-heterocyclic refers to an alkyl group that has a heterocyclic substituent.

The term alkene, as referred to herein, and unless otherwise specified, refers to an alkene group of $C_2$ to $C_{10}$, and specifically includes vinyl and allyl.

The term alkyne, as referred to herein, and unless otherwise specified, refers to an alkyne group of $C_2$ to $C_{10}$.

As used herein, "diketopiperazines" includes diketopiperazines and derivatives and modifications thereof falling within the scope of the above-general formula.

Fumaryl diketopiperazine is most preferred for pulmonary applications.

(ii). Synthesis

Diketopiperazines can be formed by cyclodimerization of amino acid ester derivatives, as described by Katchalski, et al., *J. Amer. Chem. Soc.* 68:879-80 (1946), by cyclization of dipeptide ester derivatives, or by thermal dehydration of amino acid derivatives in high-boiling solvents, as described by Kopple, et al., *J. Org. Chem.* 32(2):862-64 (1968), the teachings of which are incorporated herein. 2,5-diketo-3,6-di (aminobutyl)piperazine (Katchalski et al. refer to this as lysine anhydride) was prepared via cyclodimerization of N-epsilon-P-L-lysine in molten phenol, similar to the Kopple method in *J. Org. Chem.*, followed by removal of the blocking (P)-groups with 4.3 M HBr in acetic acid. This route is preferred because it uses a commercially available starting material, it involves reaction conditions that are reported to preserve stereochemistry of the starting materials in the product and all steps can be easily scaled up for manufacture.

Diketomorpholine and diketooxetane derivatives can be prepared by stepwise cyclization in a manner similar to that disclosed in Katchalski, et al., *J. Amer. Chem. Soc.* 68:879-80 (1946).

Diketopiperazines can be radiolabelled. Means for attaching radiolabels are known to those skilled in the art. Radiolabelled diketopiperazines can be prepared, for example, by reacting tritium gas with those compounds listed above that contain a double or triple bond. A carbon-14 radiolabelled carbon can be incorporated into the side chain by using $^{14}$C labeled precursors which are readily available. These radiolabelled diketopiperazines can be detected in vivo after the resulting microparticles are administered to a subject.

(a) Synthesis of Symmetrical Diketopiperazine Derivatives

The diketopiperazine derivatives are symmetrical when both side chains are identical. The side chains can contain acidic groups, basic groups, or combinations thereof.

One example of a symmetrical diketopiperazine derivative is 2,5-diketo-3,6-di(4-succinylaminobutyl)piperazine. 2,5-diketo-3,6-di(aminobutyl) piperazine is exhaustively succinylated with succinic anhydride in mildly alkaline aqueous solution to yield a product which is readily soluble in weakly alkaline aqueous solution, but which is quite insoluble in acidic aqueous solutions. When concentrated solutions of the compound in weakly alkaline media are rapidly acidified under appropriate conditions, the material separates from the solution as microparticles.

Other preferred compounds can be obtained by replacing the succinyl group(s) in the above compound with glutaryl, maleyl or fumaryl groups.

(b) Synthesis of Asymmetrical Diketopiperazine Derivatives

One method for preparing unsymmetrical diketopiperazine derivatives is to protect functional groups on the side chain, selectively deprotect one of the side chains, react the deprotected functional group to form a first side chain, deprotect the second functional group, and react the deprotected functional group to form a second side chain.

Diketopiperazine derivatives with protected acidic side chains, such as cyclo-Lys(P)Lys(P), wherein P is a benzyloxycarbonyl group, or other protecting group known to those skilled in the art, can be selectively deprotected. The protecting groups can be selectively cleaved by using limiting reagents, such as HBr in the case of the benzyloxycarbonyl group, or fluoride ion in the case of silicon protecting groups, and by using controlled time intervals. In this manner, reaction mixtures which contain unprotected, monoprotected and di-protected diketopiperazine derivatives can be obtained. These compounds have different solubilities in various solvents and pH ranges, and can be separated by selective precipitation and removal. An appropriate solvent, for example, ether, can then be added to such reaction mixtures to precipitate all of these materials together. This can stop the deprotection reaction before completion by removing the diketopiperazines from the reactants used to deprotect the protecting groups. By stirring the mixed precipitate with water, both the partially and completely reacted species can be dissolved as salts in the aqueous medium. The unreacted starting material can be removed by centrifugation or filtration. By adjusting the pH of the aqueous solution to a weakly alkaline condition, the asymmetric monoprotected product containing a single protecting group precipitates from the solution, leaving the completely deprotected material in solution.

In the case of diketopiperazine derivatives with basic side chains, the basic groups can also be selectively deprotected. As described above, the deprotection step can be stopped before completion, for example, by adding a suitable solvent to the reaction. By carefully adjusting the solution pH, the deprotected derivative can be removed by filtration, leaving the partially and totally deprotected derivatives in solution. By adjusting the pH of the solution to a slightly acidic condition, the monoprotected derivative precipitates out of solution and can be isolated.

Zwitterionic diketopiperazine derivatives can also be selectively deprotected, as described above. In the last step, adjusting the pH to a slightly acidic condition precipitates the monoprotected compound with a free acidic group. Adjusting the pH to a slightly basic condition precipitates the monoprotected compound with a free basic group.

Limited removal of protecting groups by other mechanisms, including but not limited to cleaving protecting groups that are cleaved by hydrogenation by using a limited amount of hydrogen gas in the presence of palladium catalysts. The resulting product is also an asymmetric partially deprotected diketopiperazine derivative. These derivatives can be isolated essentially as described above.

The monoprotected diketopiperazine is reacted to produce a diketopiperazine with one sidechain and protecting group. Removal of protecting groups and coupling with other side chains yields unsymmetrically substituted diketopiperazines with a mix of acidic, basic, and zwitterionic sidechains.

Other materials that exhibit this response to pH can be obtained by functionalizing the amide ring nitrogens of the diketopiperazine ring.

C. Transport Enhancers

In a preferred embodiment, the active agent is complexed with a transport enhancer which is degradable and capable of forming hydrogen bonds with the target biological membrane in order to facilitate transport of the agent across the membrane. The transport enhancer also is capable of forming hydrogen bonds with the active agent, if charged, in order to mask the charge and facilitate transport of the agent across the membrane. A preferred transport enhancer is diketopiperazine.

The transport enhancer preferably is biodegradable and may provide linear, pulsed or bulk release of the active agent. The transport enhancer may be a natural or synthetic polymer and may be modified through substitutions or additions of chemical groups, including alkyly, alkylene, hydroxylations, oxidations, and other modifications routinely made by those skilled in the art.

A preferred transport enhancer is fumaryl diketopiperazine. Other diketopiperazines which may be useful as a transport enhancer are described above.

Like most proteins and peptides, insulin is a charged molecule, which impedes its ability to cross charged biological membranes. It has been found that when insulin hydrogen bonds to fumaryl diketopiperazine, the charge of the peptide is masked, thereby facilitating or enhancing the passage of insulin across the membranes, such as mucosal membranes, and into the blood.

II. Methods

A. Encapsulation

In one embodiment, active agent is encapsulated within microparticles by dissolving a diketopiperazine with acidic side chains in bicarbonate or other basic solution, adding the active agent in solution or suspension, and then precipitating the microparticle by adding acid, such as 1 M citric acid.

In another embodiment, active agent is encapsulated within microparticles by dissolving a diketopiperazine with basic side chains in an acidic solution, such as 1 M citric acid, adding the active agent in solution or suspension, and then precipitating the microparticle by adding bicarbonate or another basic solution.

In still another embodiment, active agent is encapsulated within microparticles by dissolving a diketopiperazine with both acidic and basic side chains in an acidic or basic solution, adding the active agent in solution or suspension to be encapsulated, then precipitating the microparticle by neutralizing the solution.

The microparticles can be stored in the dried state and suspended for administration to a patient. In the first embodiment, the reconstituted microparticles maintain their stability in an acidic medium and dissociate as the medium approaches physiological pH in the range of between 6 and 14. In the second embodiment, suspended microparticles maintain their stability in a basic medium and dissociate at a pH of between 0 and 6. In the third embodiment, the reconstituted microparticles maintain their stability in an acidic or basic medium and dissociate as the medium approaches physiological pH in the range of pH between 6 and 8.

The impurities typically are removed when the microparticles are precipitated. However, impurities also can be removed by washing the particles to dissolve the impurities. A preferred wash solution is water or an aqueous buffer. Solvents other than water also can be used to wash the microspheres or precipitate the diketopiperazines, in order to remove impurities that are not water soluble. Any solvent in which neither the cargo nor the fumaryl diketopiperazine is soluble are suitable. Examples include acetic acid, ethanol, and toluene.

In an alternative embodiment, microparticles of diketopiperazine are prepared and provided in a suspension, typically an aqueous suspension, to which a solution of the active agent then is added. The suspension is then lyophilized or freeze dried to yield diketopiperazine microparticles having a coating of active agent. In a preferred embodiment, the active agent is insulin in a hexameric form. Zinc ions can then be removed by washing the microparticles with an appropriate solvent.

As used herein, the term "entrapped" with reference to an active agent in/with a diketopiperazine includes coating of the active agent onto microparticles of the diketopiperazine.

The diketopiperazine microparticles have been found to have a higher affinity for insulin than does zinc. Insulin has been found to be stabilized within an ordered lattice array of fumaryl diketopiperazine. In this state, in the sufficient absence of zinc ions, the insulin is predominately dimeric and monomeric, as opposed to it hexameric state. The insulin therefore more readily dissociates to its monomeric state, which is the state in which insulin exerts its biological activity.

Other complexing agents may be substituted for the diketopiperazine. Other representative complexing agents include serum albumin and other proteins, alginic acid, antibodies, cyclodextrins, phospholipids, and lecithin. For example, insulin contaminated with zinc can be complexed with bovine serum albumin. The complex can be dialyzed in tubing with a molecular weight cut-off below 1,000 Daltons to separate and remove the zinc. Once sufficient amounts of zinc have been dialyzed away, as evidenced by its presence in the dialysate, the dispersion is transferred to dialysis tubing with a molecular weight cut-off below 10,000 Daltons. Only monomeric insulin will pass through the tubing into the dialysate, leaving any remaining hexameric zinc complexed insulin behind. The purified insulin can be captured from the dialysate.

These materials may not, however, provide sufficient stabilization of unstable or labile drugs.

B. Administration

The compositions of active agent described herein can be administered to patients in need of the active agent. The compositions preferably are administered in the form of microparticles, which can be in a dry powder form for pulmonary administration or suspended in an appropriate pharmaceutical carrier, such as saline.

The microparticles preferably are stored in dry or lyophilized form until immediately before administration. The microparticles then can be administered directly as a dry powder, such as by inhalation using, for example, dry powder inhalers known in the art. Alternatively, the microparticles can be suspended in a sufficient volume of pharmaceutical carrier, for example, as an aqueous solution for administration as an aerosol.

The microparticles also can be administered via oral, subcutaneous, and intraveneous routes.

The compositions can be administered to any targeted biological membrane, preferably a mucosal membrane of a patient. In a preferred embodiment, the patient is a human suffering from Type II diabetes. In a preferred embodiment, the composition delivers insulin in biologically active form to the patient, which provides a spike of serum insulin concentration which simulates the normal response to eating.

In a preferred embodiment, hexameric insulin is entrapped in fumaryl diketopiperazine to form a solid precipitate of monomeric insulin in the fumaryl diketopiperazine, which then is washed with aqueous solution to remove the free zinc. This formulation demonstrates blood uptake following pulmonary administration at a rate 2.5 times the rate of insulin uptake following subcutaneous injection, with peak blood levels occurring at between 7.5 and 10 minutes after administration.

The range of loading of the drug to be delivered is typically between about 0.01% and 90%, depending on the form and size of the drug to be delivered and the target tissue. In a preferred embodiment using diketopiperazines, the preferred range is from 0.1% to 50% loading by weight of drug. The appropriate dosage can be determined, for example, by the amount of incorporated/encapsulated agent, the rate of its release from the microparticles, and, in a preferred embodiment, the patient's blood glucose level.

One preferred application is in the treatment of hyperinsulinemia. In a preferred embodiment, microparticles of the composition wherein the active agent is glucagon can be administered by continuous subcutaneous infusion. Glucagon is an extremely unstable peptide, but can be stabilized in particles of diketopiperazine, for example. The stabilized glucagon/diketopiperazine microparticles can be made by adding glucagon to a solution of diketopiperazine which hydrogen bonds to the glucagon and when the solution is acidified, such as by adding a food acid, both the diketopiperazine and the glucagon self-assemble to form uniform microspheres having a mean particle size of, for example, about 2 μm. In this process, approximately 95% of the glucagon is pulled out of solution and is evenly distributed within the diketopiperazine microparticle. These particles can readily be suspended and infused subcutaneously with a standard infusion pump. Then the glucagon/diketopiperazine particles are contacted with the near neutral pH environment of the subcutaneous fluid, where they dissolve, thereby releasing glucagon in its pharmacologically active state.

The compositions and methods described herein are further described by the following non-limiting examples.

EXAMPLE 1

Removal of Zinc from U.S.P. Injectable Insulin

Insulin trapped in fumaryl diketopiperazine was analyzed to assess whether zinc was removed during the entrapment process. The insulin used as the starting material met U.S.P. standards for injectable insulin, and according to the certificate of analysis, the insulin contained a considerable quantity of zinc: 0.41%. This insulin was then entrapped in fumaryl diketopiperazine to form a solid fumaryl diketopiperazine/insulin mixture, as described above.

Following entrapment of the insulin in fumaryl diketopiperazine, the amount of zinc theoretically should be present in the same proportion as it existed in the neat insulin. Using the certificate of analysis value, it was calculated that one should expect to find 697 parts per million (ppm) of zinc per gram in the solid yield of fumaryl diketopiperazine/insulin. Surprisingly, the quantity of zinc present the solid fumaryl diketopiperazine/insulin was measured to be only 6 ppm. The "missing" zinc was presumably eliminated with the water used to wash the insulin/fumaryl diketopiperazine precipitate.

EXAMPLE 2

Bioavailability of Insulin in Diketopiperazine Pulmonary Formulation

Subjects and Methods

The study was reviewed and approved by the ethical review committee of the Heinrich-Heine-University, Düsseldorf, and conducted according to local regulations, the Declaration of Helsinki and the rules of Good Clinical Practice.

The study was conducted with 5 healthy male volunteers. Inclusion criteria were good health, as judged by physical examination, age: 18 to 40 years, body mass index: 18 to 26 kg/m$^2$, capability to reach peak inspiratory flow of ≧4 l/sec measured by a computer assisted spirometry and a FEV$_1$ equal to or greater than 80% of predicted normal (FEV$_1$=forced expiratory volume in one second). Exclusion criteria were Diabetes mellitus type 1 or 2, prevalence of human insulin antibodies, history of hypersensitivity to the study medication or to drugs with similar chemical structures, history or severe or multiple allergies, treatment with any other investigational drug in the last 3 months before study entry, progressive fatal disease, history of drug or alcohol abuse, current drug therapy with other drugs, history significant cardiovascular, respiratory, gastrointestinal, hepatic, renal, neurological, psychiatric and/or hematological disease, ongoing respiratory tract infection or subjects defined as being smokers with evidence or history of tobacco or nicotine use.

Conduct of the Study

On the morning of the study days, the subjects came to the hospital (fasting, except for water, from midnight onward) at 7:30 a.m. The subjects were restricted from excessive physical activities and an intake of alcohol for 24 hours before each treatment day. They were randomly assigned to one of the three treatment arms. The subjects received a constant intravenous regular human insulin infusion, which was kept at 0.15 mU min$^{-1}$ kg$^{-1}$ so that serum insulin concentrations were established at 10-15 µU/ml during a period of 2 hours before time point 0. This low-dose infusion was continued throughout the test to suppress endogenous insulin secretion. Blood glucose was kept constant at a level of 90 mg/dl throughout the glucose clamp by a glucose controlled infusion system (BIOSTATOR™). The glucose clamp algorithm was based on the actual measured blood glucose concentration and the grade of variability in the minutes before to calculate the glucose infusion rates for keeping the blood glucose concentration constant. The insulin application (5 U i.v. or 10 U s.c. injection or three deep breaths inhalation per capsule (2 capsules with 50 U each) applied with a commercial inhalation device (Boehringer Ingelheim)) had to be finished immediately before time point 0. The duration of the clamp experiment was 6 hours from time point 0. Glucose infusion rates, blood glucose, serum-insulin and C-peptide were measured.

Bioefficacy and Bioavailability

To determine bioefficacy, the areas under the curve of the glucose infusion rates were calculated for the first 3 hours (AUC$_{0-180}$) after the administration and for the overall observation period of six hours after the administration (AUC$_{0-360}$) and were correlated to the amount of insulin applied. To determine bioavailability, the areas under the curve of the insulin concentrations were calculated for the first 3 hours (AUC$_{0-180}$) after the administration and for the overall observation period of six hours after the administration (AUC$_{0-360}$) and correlated to the amount of insulin applied.

In this clamp study, inhalation of 100 U of TECHNOSPHERE™/Insulin was well tolerated and was demonstrated to have a substantial blood glucose lowering effect with a relative bioavailability of 25.8% for the first three hours as calculated from the achieved serum insulin concentrations. TECHNOSPHERES™ are microparticles (also referred to herein as microspheres) formed of diketopiperazine that of self-assembles into an ordered lattice array at particular pHs, typically a low pH. They typically are produced to have a mean diameter between about 1 and about 5 µm.

Results

Figure 1B:
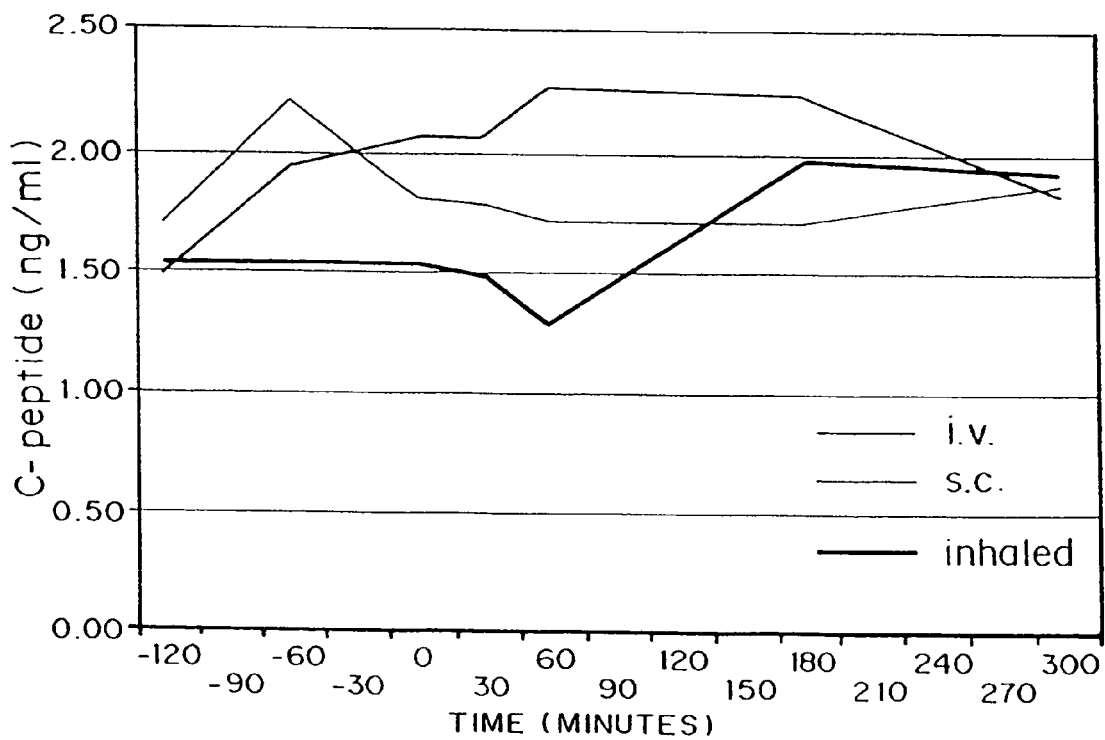
FIG. 1b is a graph of mean C-peptide concentrations during experiments comparing levels of C-peptide (ng/ml) over time (minutes) when insulin was administered intravenously, subcutaneously, and by inhalation.
Figure 2A:
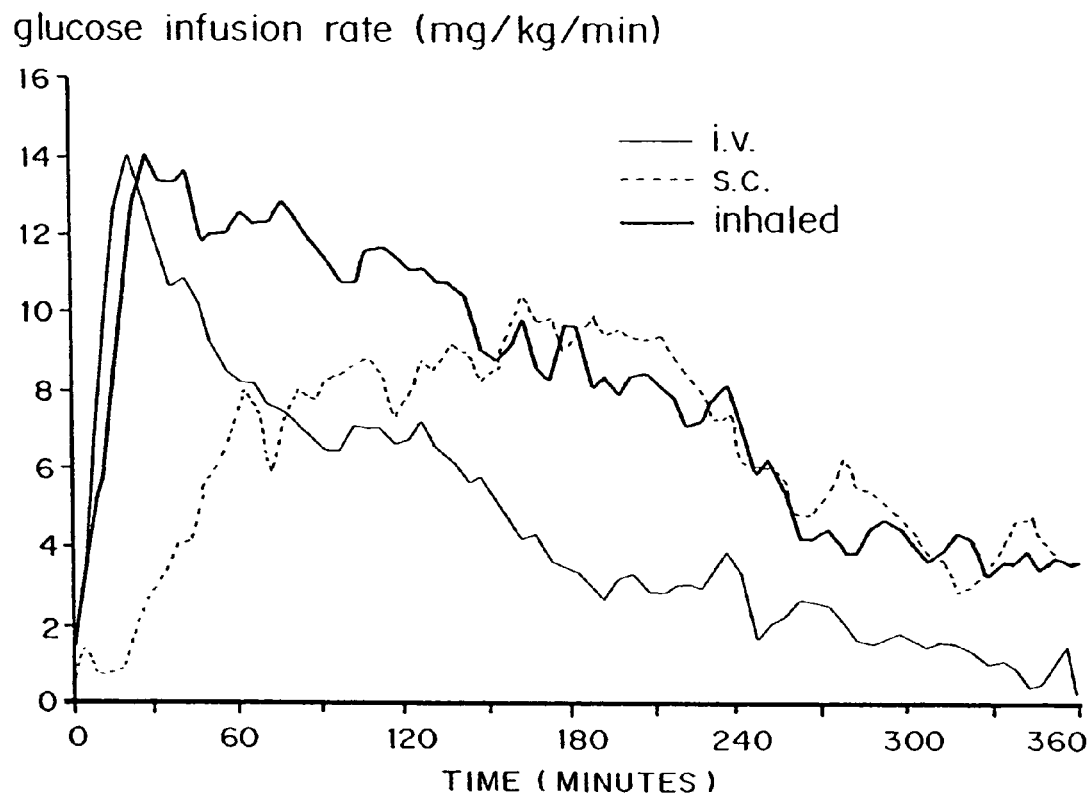
FIG. 2a is a graph of glucose infusion rate (mg/kg/min) over time (minutes) comparing insulin administered intravenously, subcutaneously, and by inhalation.
Figure 2B:
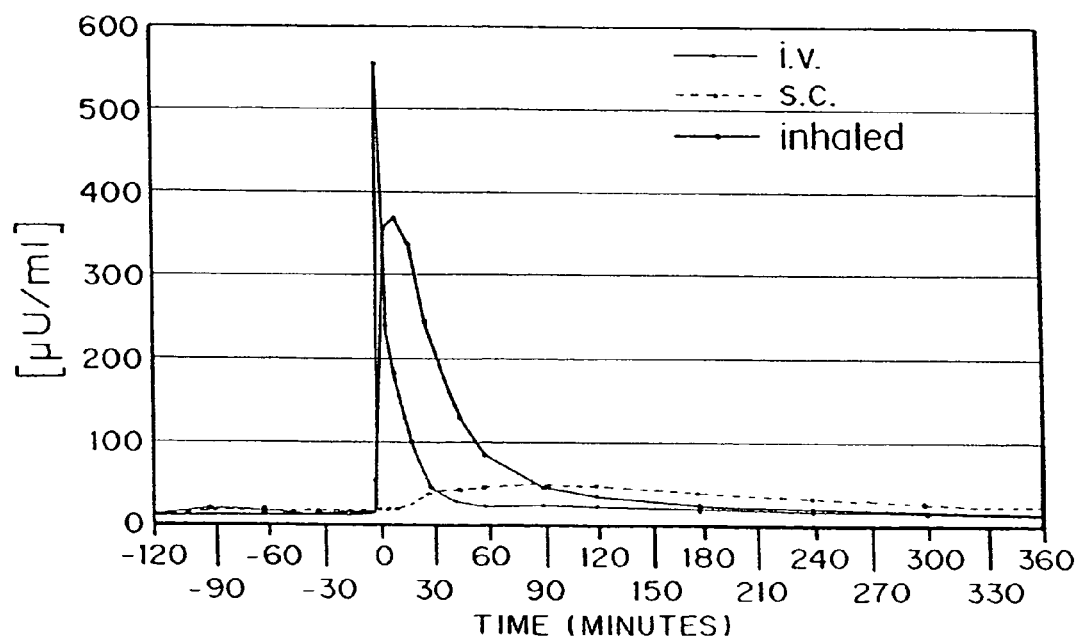
FIG. 2b is a graph of mean insulin concentrations (μU/ml) over time (minutes) comparing insulin administered intravenously, subcutaneously, and by inhalation.

The pharmacokinetic results are illustrated in FIGS. 1 and 2 and in Table 1.

Efficacy Results

Inhalation of 100 U of TECHNOSPHERE™m/Insulin (inhalation of 100 U) revealed a peak of insulin concentration after 13 min (intravenous (i.v.) (5U): 5 min, subcutaneous (s.c.) (10 U): 121 min) and a return of the insulin levels to baseline after 180 min (i.v.: 60 min, s.c. 360 min). Biological action as measured by glucose infusion rate peaked after 39 min (i.v. 14 min, s.c.: 163 min) and lasted for more than 360 min (i.v.: 240 min, s.c.: >360 min). Absolute bioavailability (comparison to i.v. application) was 14.6±5.1% for the first 3 hours and 15.5±5.6% for the first 6 hours. Relative bioavailability (comparison to s.c. application) was 25.8±11.7% for the first 3 hours and 16.4±7.9% for the first 6 hours.

TABLE 1

Pharmacokinetic Parameters

|  | Intravenous Administration | Inhaled | Subcutaneous Administration |
|---|---|---|---|
| Parameter Calculated on Glucose Infusion Rate |  |  |  |
| T50%* | 9 min | 13 min | 60 min |
| Tmax | 14 min | 39 min | 163 min |
| T-50%** | 82 min | 240 min | 240 min |
| T to baseline | 240 min | >360 min | >360 min |
| Parameter Calculated on Insulin Levels |  |  |  |
| T50%* | 2 min | 2.5 min | 27 min |
| Tmax | 5 min | 13 min | 121 min |
| T-50%** | 6 min | 35 min | 250 min |
| T to baseline | 60 min | 180 min | 360 min |

*time from baseline to half-maximal values
**time from baseline to half-maximal after passing Tmax Safety Results TECHNOSPHERE™/Insulin was shown to be safe in all patients. One patient was coughing during the inhalation without any further symptoms or signs of deterioration of the breathing system.

Conclusions

Inhalation of 100 U of TECHNOSPHERE™/Insulin was well tolerated and was demonstrated to have a substantial blood glucose lowering effect with a relative bioavailability of 25.8% for the first 3 hours as calculated from the achieved serum insulin concentrations.

Summary

In this study, the inhalation of TECHNOSPHERE™/Insulin (the formulation of example 1) was demonstrated in healthy human subjects to have a time-action profile with a rapid peak of insulin concentration (Tmax: 13 min) and rapid onset of action (Tmax: 39 min) and a sustained action over more than 6 hours. The total metabolic effect measured after inhalation of 100 U of TECHNOSPHERE™/Insulin was larger than after subcutaneous injection of 10 U of insulin. The relative bioefficacy of TECHNOSPHERE™/Insulin was calculated to be 19.0%, while the relative bioavailability was determined to be 25.8% in the first three hours.

The data also show that inhalation of TECHNOSPHERE™/Insulin resulted in a much more rapid onset of action than s.c. insulin injection that was close to the onset of action of i.v. insulin injection, while duration of action of TECHNOSPHERE™/Insulin was comparable to that of s.c. insulin injection.

The drug was well tolerated and no serious adverse events were reported during the entire trial.

EXAMPLE 3

Removal of Impurity from Proprietary Peptide

A proprietary peptide containing an impurity was trapped in fumaryl diketopiperazine, forming a peptide/fumaryl diketopiperazine precipitate. The precipitate was washed with water to remove the impurity. The peptide is rather unstable and trapping it in fumaryl diketopiperazine markedly improves its stability; both as a dry powder and in aqueous suspension for injection.

EXAMPLE 4

Stabilized Glucagon Formulations

Formulation

Glucagon was formulated under sterile conditions, into a stabilized complex by precipitation in acidic solution with fumaryl diketopiperazine (3,6bis[N-fumaryl-N-(n-butyl)amino]-2,5-diketopiperazine). The complex was washed and lyophilized, yielding a sterile dry powder formulation of diketopiperazine/glucagon (hereinafter referred to as "TG") containing from 1.2 to 8.2% glucagon by weight, depending upon the formulation parameters desired (allowing physicians to increase dose yet keep the volume constant). The TG powder was suspended in an appropriate media suitable for subcutaneous delivery in a MiniMed 507C infusion pump.

Stability Protocol

Glucagon and TG were suspended in infusion media and incubated at 40° C. in a water bath for varying amounts of time up to 150 hours.

Glucagon HPLC Analysis

An adaptation of USP method for glucagon analysis was employed. A Waters Symmetry Shield RP8 column (5 μm, 3.9×150 mm) and guard RP8 column (5 μm, 3.9×20 mm) were used at a flow rate of 1 mL/min. and a detection wavelength of 214 nm. The gradient method consisted of mobile phase A: 9.8 g $NaH_2PO_4$ (0.0816 M) and 170 mg L-cysteine (1.4 mM) per liter HPLC grade water, adjusted pH to 2.6 with phosphoric acid; and B: acetonitrile. Glucagon solutions were diluted as needed with water and injected. TG samples were prepared by adding $1/10^{th}$ volume 1 M Tris pH 10.0 to sample to solubilize the fumaryl diketopiperazine.

Rat Study Protocol

Sprague Dawley rats 200-250 g were fasted overnight and given subcutaneous injection of glucagon or TG (0.75 mg/kg) in an appropriate media that had been held at 25° C. for 0, 24, or 48 hours. Blood samples were taken at −10, −5, 0, 5, 10, 15, 20, 30, 45, and 60 minutes post dose and analyzed for blood glucose (HemCue B-glucose analyzer, Hemocue AB, Angelholm Sweden). Mean baseline was determined (pre-dose measurements) and was subtracted from the subsequent data and plotted vs. time. This was done to assure that the TG formulation, which appeared to not degrade significantly, showed appropriate pharmacological activity.

Results

Following 40° C. incubation, HPLC analysis showed an increase in breakdown products in the glucagon preparation. By contrast, TG has only one minor degradation peak (RT=6) which correlated with the slightly less active oxidative form of glucagon. Glucagon without diketopiperazine (i.e. without TECHNOSPHERES™) had many degradation peaks, some of which contributed to an enhanced effect and others that reduced the potency of glucagon.

The TG sterile lyophilized powder was shipped frozen to a hospital, where it was re-suspended in sterile media. The material re-suspended well and each vial was continuously infused over a 72 hour period.

CONCLUSION

Standard preparations of glucagon are not suitable for regulation of blood glucose by continuous subcutaneous infusion. Administration of such preparations containing variable amounts of the deamidated and hydrolysed forms resulted in highly variable blood glucose levels. Suspensions of TECHNOSPHERES™/glucagon, which is stabilized, does not aggregate and contains clinically irrelevant amounts of breakdown products. As such TG can be and has been used as a therapy for hyperinsulinemia, providing consistent, elevated glucose levels when administered subcutaneously over time.

Modifications and variations of the present invention will be obvious to those of skill in the art from the foregoing detailed description. Such modifications and variations are intended to come within the scope of the following claims.

We claim:

1. A method for delivering monomeric or dimeric insulin to a patient in need thereof, comprising administering to the patient a delivery formulation for the monomeric or dimeric insulin comprising an effective amount of insulin complexed with a diketopiperazine derivative, wherein the delivery formulation is prepared by complexing the insulin with microparticles of the diketopiperazine derivative by the steps of:
   a) providing pre-formed microparticles of the diketopiperazine derivative in a suspension comprising a solvent;
   b) adding insulin to said suspension; and
   c) removing solvent from said suspension;
   wherein the diketopiperazine derivative has the formula 2,5-diketo-3,6-di(4-X-aminobutyl)piperazine, wherein X is selected from the group consisting of fumaryl, succinyl, maleyl, and glutaryl, and
   wherein the microparticles release monomeric or dimeric insulin upon dissociation.

2. The method of claim 1 wherein X is fumaryl.

3. The method of claim 1 wherein X is succinyl.

4. The method of claim 1 wherein X is maleyl.

5. The method of claim 1 wherein X is glutaryl.

6. The method of claim 1 wherein the composition is in a dry powder form administered to the lungs via inhalation.

7. The method of claim 1 wherein the patient is a Type II diabetic.

8. The method of claim 7 wherein the composition is administered concurrently with or less than 20 minutes prior to the patient eating a meal.

9. The method of claim 1 wherein the composition is provided in one or more unit doses of insulin, each dose equivalent to about 6 IU of insulin.

10. The method of claim 1 wherein said solvent is an aqueous solvent.

11. The method of claim 1 wherein said solvent is removed by lyophilizing or freeze drying.

* * * * *